United States Patent [19] [11] 3,997,663
Pinnert et al. [45] Dec. 14, 1976

[54] ANTIBIOTIC DAUNORUBICIN AND ITS PREPARATION

[75] Inventors: Sylvie Pinnert; Leon Ninet; Jean Preud'Homme, all of Paris, France

[73] Assignee: Rhone-Poulenc S.A., Paris, France

[22] Filed: Dec. 11, 1972

[21] Appl. No.: 313,790

Related U.S. Application Data

[63] Continuation of Ser. No. 777,876, Nov. 21, 1968, which is a continuation-in-part of Ser. No. 280,816, May 16, 1963, Pat. No. 3,801,232.

[30] Foreign Application Priority Data

May 18, 1962 France .......................... 62.898076

[52] U.S. Cl. ................................ 424/120; 424/119
[51] Int. Cl.² ....................................... A61K 35/74
[58] Field of Search .................. 424/120, 119, 121

[56] References Cited

OTHER PUBLICATIONS

The Merck Index, 8th Edition, 1968, Merck & Co., Inc., Rahway, N.J., p. 322.

Primary Examiner—Jerome D. Goldberg
Attorney, Agent, or Firm—Stevens, Davis, Miller & Mosher

[57] ABSTRACT

The invention provides the novel antibiotic known as daunorubicin (13057 RP) which has a powerful anticancer effect and is also an anti-bacterial agent. This antibiotic is a constituent of a mixture of three antibiotics, called 9865 R.P., produced by aerobic culture of one of the strains of Streptomyces, NRRL 3046 and 3045.

4 Claims, 10 Drawing Figures

ANTIBIOTIC DAUNORUBICIN AND ITS PREPARATION

This application is a continuation of our prior copending application Ser. No. 777,876, filed Nov. 21, 1968, which in turn is a continuation-in-part of our prior copending application Ser. No. 280,816, filed May 16, 1963 now U.S. Pat. No. 3,801,232.

This invention relates to antibiotics and their preparation.

The present invention provides the new antibiotic mixture hereinafter designated 9865 RP, and its three constituents, hereinafter designated 13057 RP, 13213 RP and 13330 RP.

9865 RP, and its three constituents, possess a very pronounced anticancer activity, they also possess a very important antibacterial effect both against Gram-positve and Gram-negative organisms. This property is all the more valuable in that they retain a high level of activity against organisms (and in particular staphylococcal strains) which have become resistant to antibiotics currently in use or to certain anticancer antibiotics, such as actinomycin and rufochromomycin.

The constituent antibiotic 13057 RP, which is known by the generic name daunorubicin and is also called rubidomycin or daunomycin, has proved to be of substantial utility in the treatment of cancerous conditions, and especially in securing remissions in cases of acute leukemia.

The new antibiotic mixture 9865 RP is produced by the culture of two microorganisms, hereinafter more completely characterised, belonging to the genus Streptomyces and designated, respectively, Steptomyces 8899 and Streptomyces 31723.

The antibiotic mixture 9865 RP has the following characteristics: it is an amorphous orange-red powder soluble in chlorinated solvents, such as chloroform and dichloroethane, moderately soluble in water acidified to between pH 3 and 4, very slightly soluble in alcohols and practically insoluble in water, benzene and diethyl ether; it contains carbon hydrogen, oxygen and nitrogen in the following proportions, as determined by analysis, C = 61.0%, H = 6.2%, O = 28.15%, M = 2.65%, its ultra-violet spectrum (as determined on a solution in 96% ethanol) shows absorption maxima at 236 m$\mu$, $E_{1\ cm.}^{1\%}$ = 425, 255 m$\mu$, $E_{1\ cm.}^{1\%}$ = 308, 290 m$\mu$, $E_{1\ cm.}^{1\%}$ = 114, and 495 m$\mu$, $E_{1\ cm.}^{1\%}$ = 146, and absorption minima at 245 m$\mu$, $E_{1\ cm.}^{1\%}$ = 284, 280 m$\mu$, $E_{1\ cm.}^{1\%}$ = 108, and 325 m$\mu$, $E_{1\ cm.}^{1\%}$ = 20, and a shoulder at 533 m$\mu$, $E_{1\ cm.}^{1\%}$ = 80; its infra-red spectrum (as determined on tablets made up with potassium bromide) shows the following principal absorption bands:

TABLE I

| | | | |
|---|---|---|---|
| about 3450 | S | 1147 | sh |
| 2925 | S | 1113 | S |
| 1715 | S | 1080 | S |
| 1615 | S | 1067 | S |
| 1580 | S | 1030 | S |
| 1445 | S | 1005 | vS |
| 1410 | vS | 990 | vS |
| 1377 | S | about 945 | sh |
| 1350 | S | 917 | m |
| 1282 | vS | 873 | m |
| 1260 | sh | 840 | m |
| 1230 | S | 815 | m |
| 1205 | vS | 793 | m |
| about 1190 | sh | 764 | m |

TABLE I-continued

| | |
|---|---|
| about 690 | m | vS = very strong
S = strong
m = medium
sh = shoulder.

The accompanying drawings show the ultra-violet and infra-red absorption spectra of 9865 RP and its three constituents. In the drawings, FIG. I is the ultra-violet spectrum of 9865 RP and
FIG. II is the infra-red spectrum of 9865 RP.
FIGS. III, V, VII and IX are the ultra-violet spectra of 13057 RP daunorubicin, the hydrochloride of 13057 RP daunorubicin, 13213 RP and the aglycone of 9865 RP, respectively, and
FIGS. IV, VI, VIII and X are the infra-red spectra of 13057 RP daunorubicin, the hydrochloride of 13057 RP daunorubicin, 13213 RP, and the aglycone of 9865 RP, respectively.

Figure 1:
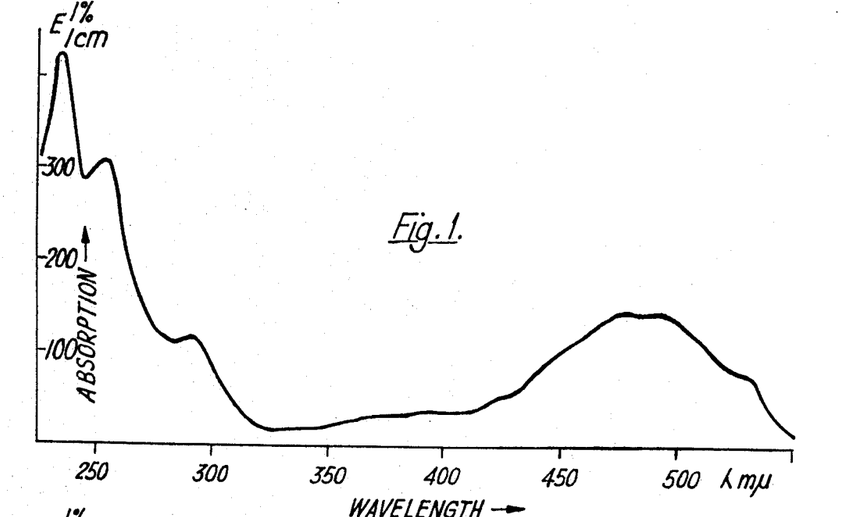
Figure 2:
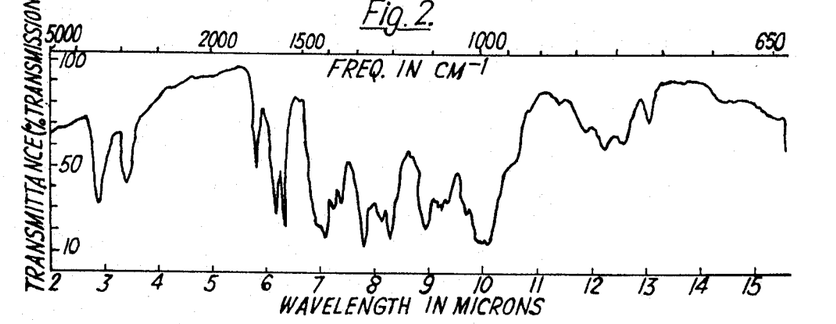
Figure 3:
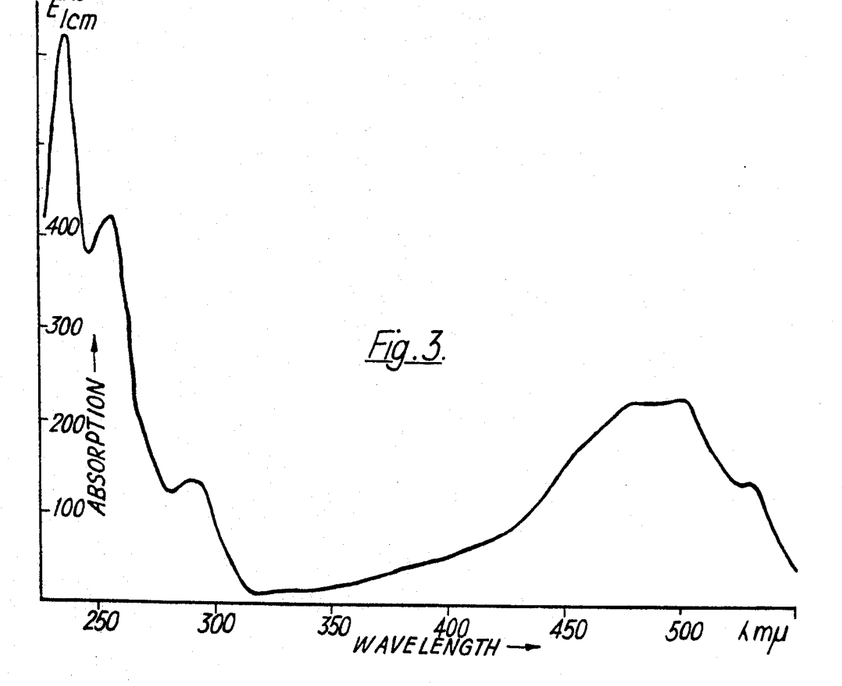
Figure 4:
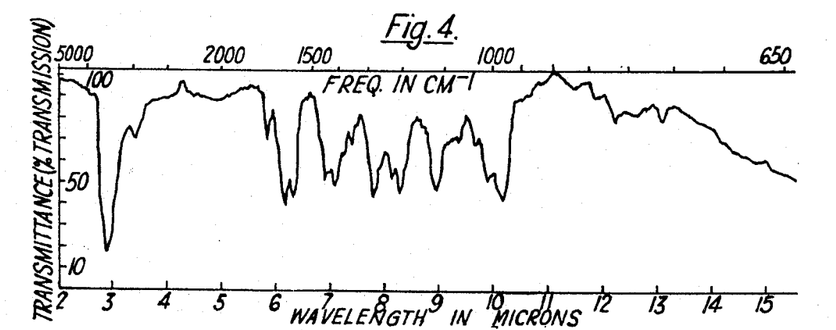
Figure 5:
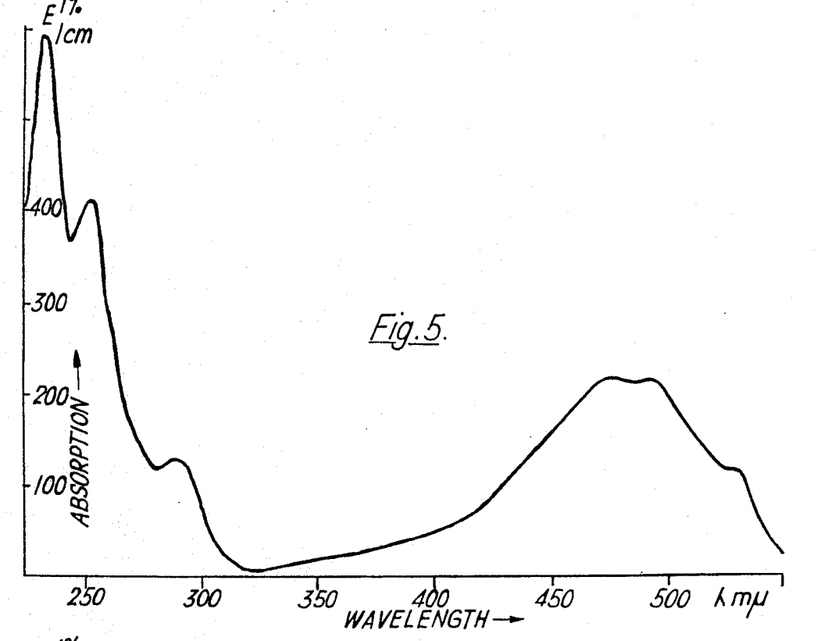
Figure 6:
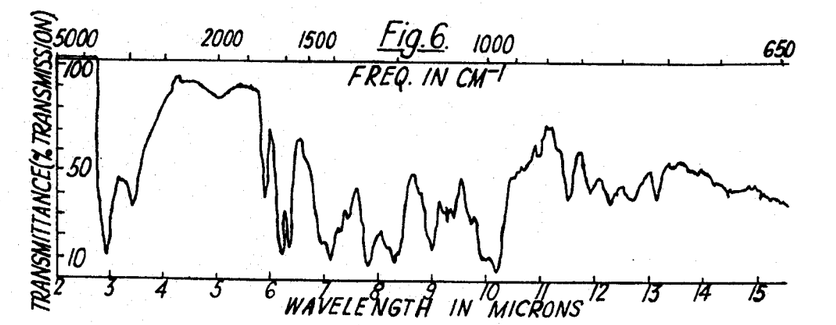
Figure 7:
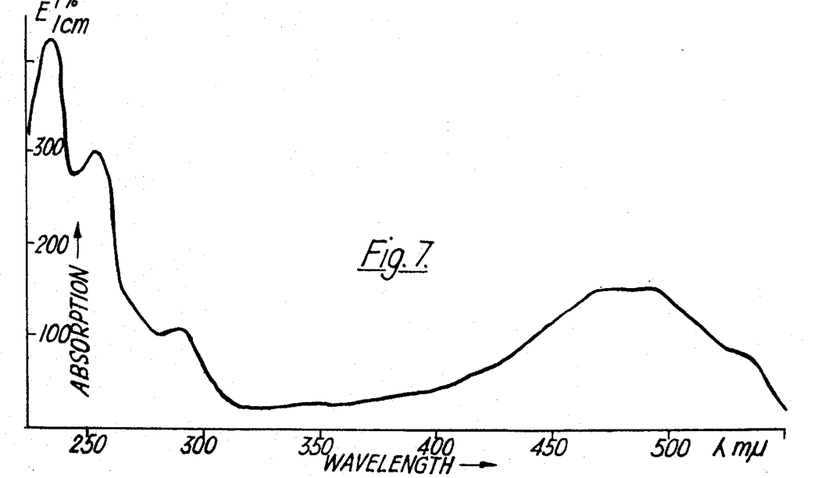
Figure 8:
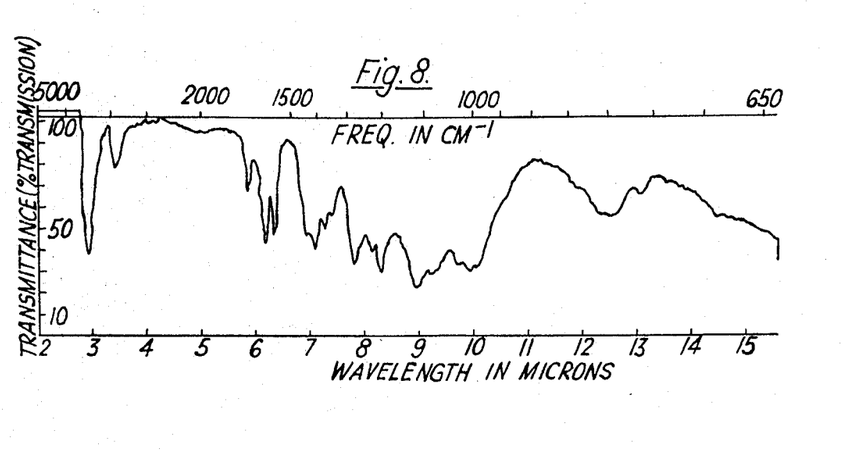
Figure 9:
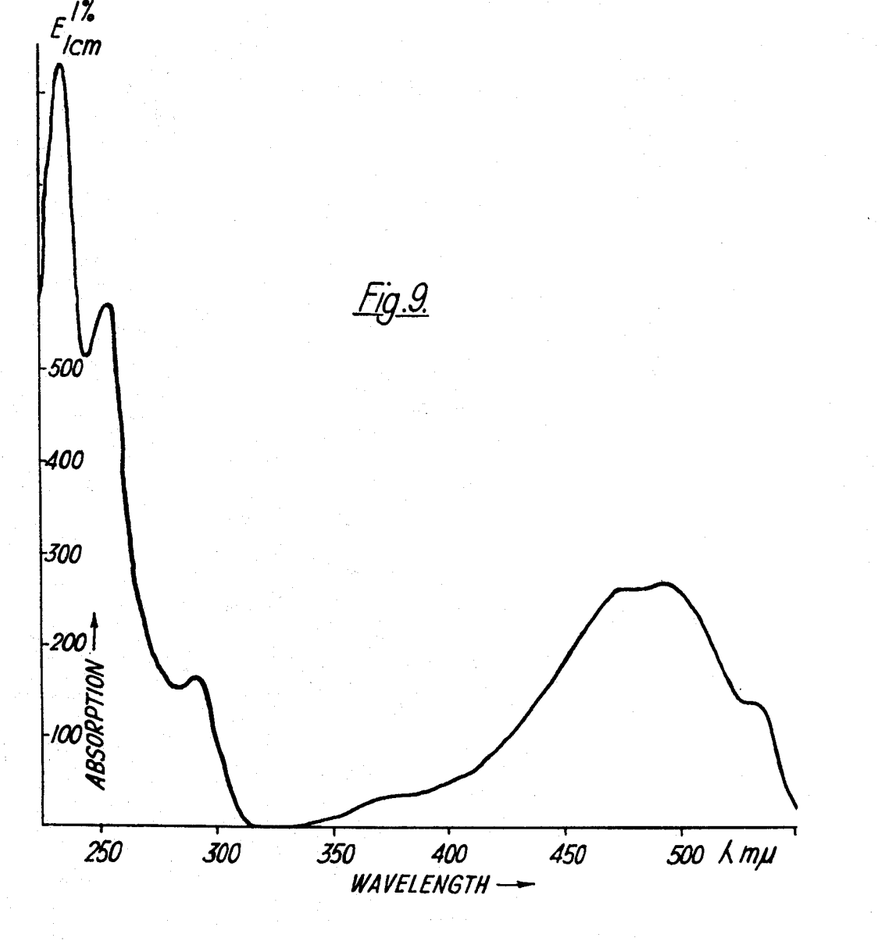
Figure 10:
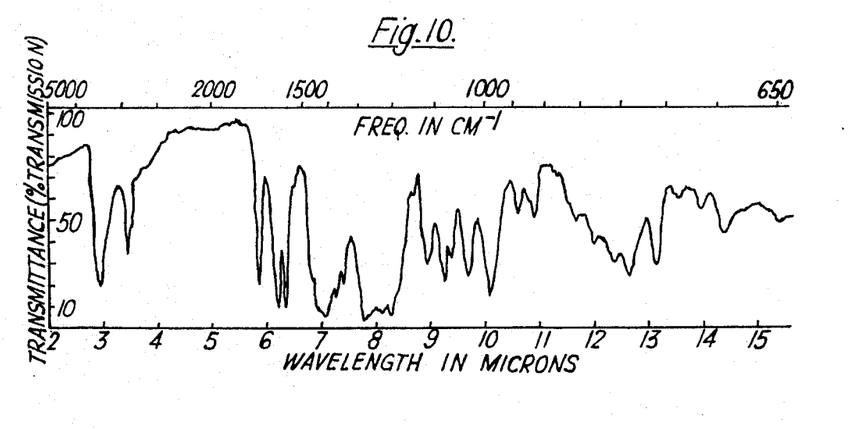

The constituents of 9865 RP can be detected by paper chromatography. The antibiotic is chromatographed on Arches No. 302 paper impregnated with a pH 4.8 phosphate buffer, with n-butanol saturated with water, using descending development. The chromatogram is developed by bioautography on nutritive agar plates seeded with *Bacillus subtilis* or *Klebsiella pneumoniae*. The chromatogram shows that 9865 RP contains three active substances, herein named 13057 RP daunorubicin, 13215 RP and 13330 RP, the Rf value of which are, in this system, respectively 0.3, 0.7 and 0.9.

These three constituents, of which 13057 RP daunorubicin is particularly important, may be isolated from 9865 RP by various methods, some of which will be described below. 13057 RP daunorubicin is a base which forms acid addition salts. The free base is an amorphous red powder soluble in alcohols and chloroform, very slightly soluble in water and ketones and practically insoluble in benzene and diethyl ether; it contains carbon, hydrogen, oxygen and nitrogen in the following proportions, as determined by analysis, C = 59.8%, H = 5.85%, N = 2.3%, O = 29.45%; it melts at 155°–170° C. (with decomposition); its ultraviolet spectrum (as determined on a solution in 96% ethanol) shows absorption maxima at 236 m$\mu$, $E_{1\ cm.}^{1\%}$ = 621, 255 m$\mu$, $E_{1\ cm.}^{1\%}$ = 426, 290–295 m$\mu$, $E_{1\ cm.}^{1\%}$ = 135, and 482–498 m$\mu$, $E_{1\ cm.}^{1\%}$ = 230, and absorption minima at 245 m$\mu$, $E_{1\ cm.}^{1\%}$ = 378, 280 m$\mu$, $E_{1\ cm.}^{1\%}$ = 122, and 325 m$\mu$, $E_{1\ cm.}^{1\%}$ = 10, and a shoulder at 533 m$\mu$, $E_{1\ cm.}^{1\%}$ = 127; its infra-red spectrum (as determined on tablets in mixture with potassium bromide) shows the following principal absorption bands:

TABLE II

| | | | | | | | |
|---|---|---|---|---|---|---|---|
| about 3450 | vS | 1410 | S | 1205 | S | 1068 | m |
| 2925 | S | 1380 | S | about 1190 | sh | 1033 | m |
| 1715 | m | 1355 | S | 1150 | sh | 1010 | S |
| 1615 | S | 1282 | S | 1117 | S | 983 | S |
| 1582 | S | 1262 | sh | 1090 | m | 950 | w |
| 1447 | S | 1230 | S | 1080 | m | 918 | w |
| 867 | w | 815 | m | 790 | m | 762 | m |
| about 840 | w | | | | | | | vS = very strong
S = strong
m = medium
w = weak
sh = shoulder;

its hydrochloride forms orange-red needles soluble in water and alcohols, slightly soluble in chloroform and practically insoluble in benzene and diethyl ether, has the following elemental composition as determined by analysis; C = 55.4%, H = 5.45%, O = 28.8%, N = 2.13%, Cl = 6.15%, melts at 225°–230° C. (with decomposition), shows the optical rotation $[\alpha]_D^{20} = +240°$ ($c = 0.1$; methanol), has an ultra-violet spectrum (as determined on a solution in 96% ethanol) showing absorption maxima at 236 m$\mu$; $E_{1\ cm.}^{1\%} = 594$, 255 m$\mu$, $E_{1\ cm.}^{1\%} = 410$, 290–295 m$\mu$, $E_{1\ cm.}^{1\%} = 129$, and 482–498 m$\mu$, $E_{1\ cm.}^{1\%} = 218$, and absorption minima at 245 m$\mu$, $E_{1\ cm.}^{1\%} = 360$, 280 m$\mu$, $E_{1\ cm.}^{1\%} = 118$, and 325 m$\mu$, $E_{1\ cm.}^{1\%} = 10$, and a shoulder at 533 m$\mu$, $E_{1\ cm.}^{1\%} = 120$, and has an infra-red spectrum (as determined on tablets in mixture with potassium bromide) showing the following principal absorption bands:

TABLE III

| | | | | |
|---|---|---|---|---|
| about 3450 | vS | 1350 S | 1080 S | 882 m |
| about 2925 | S | 1282 vS | 1064 S | 867 S |
| 1707 | S | 1260 sh | 1028 S | 838 S |
| 1610 | vS | 1228 S | 1000 vS | 813 S |
| 1575 | vS | 1205 vS | 982 vS | 788 S |
| 1439 | vS | about 1190 sh | 950 m | 762 S |
| 1408 | vS | about 1145 sh | 935 m | about 692 m |
| 1370 | S | 1112 vS | 912 m | | vS = very strong
S = strong
m = medium
sh = shoulder.

13213 RP is an amorphous orange-red powder soluble in chlorinated solvents, such as chloroform, and in dimethylformamide, moderately soluble in water acidified to between pH 3 and 4, very slightly soluble in alcohols and practically insoluble in water, benzene and diethyl ether; it contains carbon, hydrogen and nitrogen in the following proportions, as determined by analysis, C = 58.6%, H = 6.2%, N = 2.2%, and also contains oxygen; it has an ultra-violet spectrum (as determined on a solution in 96% ethanol) showing absorption maxima at 236 m$\mu$, $E_{1\ cm.}^{1\%} = 425$, 255 m$\mu$, $E_{1\ cm.}^{1\%} = 297$, 290–295 m$\mu$, $E_{1\ cm.}^{1\%} = 108$, and 480–495 m$\mu$, $E_{1\ cm.}^{1\%} = 155$, and absorption minima at 245 m$\mu$, $E_{1\ cm.}^{1\%} = 274$, 280 m$\mu$, $E_{1\ cm.}^{1\%} = 103$, and 325 m$\mu$, $E_{1\ cm.}^{1\%} = 20$, and a shoulder at 533 m$\mu$, $E_{1\ cm.}^{1\%} = 90$; and its infra-red spectrum (as determined on tablets in mixture with potassium bromide) shows the following principal absorption bands:

TABLE IV

| | | | | |
|---|---|---|---|---|
| about 3450 | S | 1377 S | about 1190 sh | 995 S |
| about 2925 | m | 1352 S | about 1180 sh | about 837 m |
| 1715 | m | 1282 S | 1117 vS | 812 S |
| 1615 | S | 1262 S | about 1080 S | about 796 S |
| 1583 | S | 1230 S | 1032 S | 765 m |
| about 1445 | S | 1205 S | 1008 S | about 690 m |
| 1412 | S | | | | vS = very strong
S = strong
m = medium
sh = shoulder.

The acid hydrolysis of 9865 RP and of its two main constituents, 13057 RP daunorubicin and 13213 RP, liberates amino-sugars and a coloured substance which is an aglycone. This aglycone forms orange-red needles, soluble in alcohols, ethyl acetate and chloroform, slightly soluble in benzene and diethyl ether, and insoluble in water; it has the following composition as determined by analysis: C = 63.4%, H = 5.7%, O = 30.4%, N = less than 0.2%, it melts at 160° C, and again at 225°–230° C.; its ultra-violet spectrum (as determined on a solution in 96% ethanol) shows absorption maxima at 236 m$\mu$, $E_{1\ cm.}^{1\%} = 835$, 255 m$\mu$, $E_{1\ cm.}^{1\%} = 570$, 290–295 m$\mu$, $E_{1\ cm.}^{1\%} = 167$, and 470–495 m$\mu$, $E_{1\ cm.}^{1\%} = 272$, and absorption minima at 245 m$\mu$, $E_{1\ cm.}^{1\%} = 510$, 280 m$\mu$, $E_{1\ cm.}^{1\%} = 149$, and 325 m$\mu$, $E_{1\ cm.}^{1\%} = $ about 0, and a shoulder at 533 m$\mu$, $E_{1\ cm.}^{1\%} = 145$; its infra-red spectrum (as determined on tablets in mixture with potassium bromide) shows the folowing principal absorption bands:

TABLE V

| | | | | |
|---|---|---|---|---|
| about 3430 | S | 1350 S | about 1083 S | 835 S |
| about 2910 | S | 1275 vS | 1065 S | 808 S |
| 1707 | S | 1228 vS | 1032 S | 790 S |
| 1610 | vS | 1210 vS | 988 vS | 762 S |
| 1575 | vS | 1185 sh | 941 m | 737 m |
| 1440 | vS | 1150 m | 918 m | 718 m |
| 1415 | vS | 1117 S | 858 m | 695 S |
| 1375 | vS | | | | vS = very strong
S = strong
m = medium
sh = shoulder.

The aglycone of 9865 RP, 13057 RP daunorubicin and 13213 RP may be identified by circular paper chromatography, which is effected on Arches No. 302 paper impregnated with a solution of acetone containing 20% formamide, with a 2:1 mixture of chloroform and benzene saturated with formamide. It is thus possible to demonstrate the existence of a single substance, having an Rf value of 0.86.

The bacteriostatic activity of 9865 RP and of 13057 RP daunorubicin and 13213 RP, in relation to a certain number of organisms, has been determined by the dilution methods currently employed for this purpose. For each organism, the lowest concentration of substance has been determined which, under the defined conditions, prevents all visible development in an appropriate nutritive broth. The results of various determinations are shown in Table VI, wherein the minimal bacteriostatic concentrations are expressed as micrograms of substance per cubic centimetre of experimental medium.

TABLE VI

| | ANTIBACTERIAL SPECTRA | | |
|---|---|---|---|
| | 9865 RP | 13057 RP daunorubicin | 13213 RP |
| Bacterial strains tested | Minimal bacteriostatic concentration mcg./cc. | Minimal bacteriostatic concentration mcg./cc. | Minimal bacteriostatic concentration mcg./cc. |
| *Staphylococcus aureus* strain 209 P - ATCC 6538 P | 0.20 | 4.3 | 0.14 |
| *Staphylococcus aureus*, Oxford strain - ATCC 9144 | 0.26 | 4.2 | 0.15 |

TABLE VI-continued
ANTIBACTERIAL SPECTRA

| Bacterial strains tested | 9865 RP Minimal bacteriostatic concentration mcg./cc. | 13057 RP daunorubicin Minimal bacteriostatic concentration mcg./cc. | 13213 RP Minimal bacteriostatic concentration mcg./cc. |
|---|---|---|---|
| Staphylococcus aureus, strain 133 (Institut Pasteur) | 0.14 | 4.2 | 0.083 |
| Staphylococcus aureus, strain B₃ (streptomycin and penicillin resistant) | 0.35 | 5.2 | 0.20 |
| Staphylococcus aureus, strain Hb (tetracycline and penicillin resistant) | 0.32 | 5.3 | 0.17 |
| Staphylococcus aureus, strain Launoy 1 (tetracycline, streptomycin, chloramphenicol and penicillin resistant) | 0.21 | 7.1 | 0.091 |
| Staphylococcus aureus, strain Launoy 2 (tetracycline, streptomycin and penicillin resistant) | 0.17 | 4.8 | 0.091 |
| Staphylococcus aureus, strain Beaujon 3 (tetracycline, streptomycin, chloramphenicol and penicillin resistant) | 0.16 | 4.4 | 0.068 |
| Staphylococcus aureus, strain 2700 R (streptothricin resistant) | 0.21 | 4.7 | 0.10 |
| Staphylococcus aureus, strain 1142 R (congocidin resistant) | 0.17 | 2.1 | 0.10 |
| Staphylococcus aureus, strain 3486 R (spiramycin resistant) | 0.21 | 5.2 | 0.091 |
| Staphylococcus aureus, carbomycin resistant strain | 0.23 | 5.3 | 0.12 |
| Staphylococcus aureus, erythromycin resistant strain | 0.11 | 3.8 | 0.055 |
| Staphylococcus aureus, chloramphenicol resistant strain | 0.08 | 4.1 | 0.045 |
| Staphylococcus aureus, novobiocin resistant strain | 0.12 | 3.9 | 0.075 |
| Staphylococcus aureus, streptogramin resistant strain | 0.16 | 1.9 | 0.076 |
| Staphylococcus aureus actinomycin resistant strain | 0.19 | 5.8 | 0.10 |
| Staphylococcus aureus strain 662 R (rufochromomycin resistant) | 0.29 | 6.3 | 0.16 |
| Micrococcus citreus - ATCC 8,411 | 0.71 | 4.2 | 0.19 |
| Micrococcus lysodeikticus | 0.21 | 2.5 | 0.068 |
| Gaffkya tetragena (Fac. Phie) | 0.44 | 6.7 | 0.23 |
| Sarcina lutea - ATCC 9341 | 0.15 | 1.2 | 0.088 |
| Sarcina alba (Fac. Phie) | 0.38 | 3.3 | 0.18 |
| Streptococcus faecalis (Thiercelin's enterococcus Fac. Phic) | 1.2 | 19 | 0.55 |
| Streptococcus faecalis - ATCC 9790 | 2.1 | 30 | 1 |
| Streptococcus viridans (Institut Pasteur) | | 43 | 2.1 |
| Streptococcus pyogenes hemolyticus (strain Dig. 7, Institut Pasteur) | 0.11 | 1.6 | 0.17 |
| Diplococcus pneumoniae (strain Til. Institut Pasteur | 0.075 | 0.89 | 0.05 |
| Neisseria catarrhalis (Fac. Phie) | 0.31 | 2.2 | 0.12 |
| Corynebacterium pseudodiphtericum (Fac. Phie) | 0.026 | 1.7 | 0.017 |
| Lactobacillus casei - ATCC 7469 | 0.035 | 1.2 | 0.017 |
| Bacillus subtilis - ATCC 6633 | 0.12 | 1.2 | 0.058 |
| Bacillus subtilis (strain Z0 5 A, Fac. Phic) | 0.12 | 1.5 | |
| Bacillus subtilis (strain 3 R 9575, Merck - ATCC 9524) | 0.12 | 1.8 | 0.052 |
| Bacillus cereus - ATCC 6630 | 0.24 | 2.2 | 0.084 |
| Bacillus brevis - ATCC 8185 | 0.14 | 1.4 | 0.083 |
| Bacillus mycoides | 0.14 | 1.8 | 0.049 |
| Bacillus megatherium (NRRL B 1125) | 0.25 | 1.3 | 0.15 |
| Bacillus polymyxa (NTCT 4747) | 0.70 | 4.4 | 0.83 |
| Mycobacterium smegmatis - ATCC 607 | 0.13 | 1.2 | 0.21 |
| Mycobacterium phlei (Bacteriological Institute of Lyon) | 0.041 | 5 | 0.035 |
| Mycobacterium para-smegmatis (A 75 - Lausanne) | 0.069 | 2.2 | 0.09 |
| Escherichia coli - ATCC 9637 | >4.3 | 500 | 5.1 |
| Shigella dysenteriae (Shiga L. - Institut Pasteur) | 16 | 2000 | 13 |
| Salmonella typhimurium (Institut Pasteur) | 31 | 1000 | 13 |
| Salmonella paratyphi A (Lacasse, Institut Pasteur) | 3.9 | 16 | |
| Salmonella schottmuelleri (paratyphi B) (Fougenc, Institut Pasteur) | 16 | 1000 | 13 |
| Bacillus lactis aerogenes (Fac. Phie) | 1.9 | 120 | |
| Aerobacter aerogenes - ATCC 8308 | 7.8 | 1000 | 6.3 |
| Acaligenes faecalis - ATCC 8749 | 0.18 | 1.8 | 0.065 |
| Proteus vulgaris (Fac. Phie) | 16 | >2000 | 25 |
| Proteus X 19 | 3.9 | 62 | 3.1 |
| Klebsiella pneumoniae - ATCC 10,031 | 1 | 8.9 | 0.88 |
| Serratia marcescens (A. 476, Lausanne) | 7.8 | 120 | 6.3 |
| Pseudomonas aeruginosa (Bass strain - Institut Pasteur) | 16 | 1000 | 12 |
| Brucella bronchiseptica (CN 387 - Wellcome Institute) | | 62 | 6.3 |
| Pasteurella multocida (A. 125 - Institut Pasteur) | 0.24 | 1.8 | 0.07 |

These results show that the bacteriostatic activity of 9865 RP, 13057 RP daunorubicin and 13213 RP is exerted against numerous bacteria, certain of which are resistant to one or more of the following antibiotics: penicillin, tetracycline, streptomycin, streptothricin, neomycin, congocidin, erythromycin, carbomycin, spiramycin, streptogramin, chloramphenicol, novobiocin, and the anticancer antibiotics, actinomycin and rufochromomycin. The anticancer activities of 9865 RP and of its three constituents have been demonstrated in the laboratory, where they have been shown to be particularly active against transplantable tumours in the mouse, such as Ehrlich's ascitic tumour, sarcoma 180, benzopyrene sarcoma and lymphoblastic leucaemia AKR. The most interesting of the new antibiotics in this respect has been shown to be 13057 RP daunorubicin, which shows in the mouse an acute 50% lethal dose (or $LD_{50}$), determined for subcutaneous administration, of $LD_{50} = 47$ mg./kg. s.c. and a subacute 50% lethal dose (or $LD_{50}$) (giving one dose per day for 5 days), determined for intravenous or subcutaneous administration, of $LD_{50} = 8.75$ mg./kg. (intravenously) or $LD_{50} = 13.65$ mg./kg. (subcutaneously).

The microorganisms which produce 9865 RP belong to the genus Streptomyces and are designated herein Streptomyces 8899 and Streptomyces 31723 respectively. They have been deposited at the Northern Regional Research Laboratory of Peoria, Ill., under the respective references NRRL 3046 and NRRL 3045. Subcultures of either of the said microorganisms can be obtained from the said depository by anyone freely and without restriction. The microorganisms were isolated from soil samples taken in two different regions of Algeria.

The method of isolation was as follows. The soil sample is suspended in sterile distilled water and the suspension diluted to various concentrations. A small volume of each dilution is spread on the surface of Petri dishes containing a nutritive agar medium. After incubation for several days at 26° C. the colonies of microorganisms which it is wished to isolate are pricked out onto agar slopes to give more abundant cultures.

According to the modern classifications designed for the identification of Streptomyces [S. A. Waksman, "The Actinomycetes," The Williams and Wilkins Company, Baltimore, 1961, Vol. II — "Bergey's Manual of Determinative Bacteriology", 7th Edition, The Williams and Wilkins Company, Baltimore, 1957 — L. Ettlinger et coll., Archiv. fur Mikrobiologie, 31, 326 (1958)] no description of any species has been found, the culture characteristics of which coincide with those of Streptomyces 8899 or 31723.

By means of the classification given by G. F. Gause et coll. ("Zur Klassifizierung der Actinomyceten", Veb Gustav Fisher Verlag, Jena, 1958) the species *Streptomyces coeruleorubidus* has nevertheless been observed as having a descritpion closely similar to that of the newly discovered strains. Although, according to S. A. Waksman (loc.cit. pp.323–326) this description is somewhat imprecise, it is nevertheless possible to assimilate Streptomyces 8899 and Streptomyces 31723 into the species *Streptomyces coeruleorubidus* and to list them under the designations *Streptomyces coeruleorubidus* strain 8899 and *Streptomyces coeruleorubidus* strain 31723 respectively. In order to clarify their similarities and differences, the detailed characteristics of the two strains Streptomyces 8899 and Streptomyces 31723 are given below parallel with the characteristics of *Streptomyces coeruleorubidus* as described by G. F. Gause et coll.

Microscopic Morphology

The sporulation of Streptomyces 8899 and 31723 is difficult to observe because of its complexity. It is observable either on "synthetic" media such as that described by Grundy et coll. (Antibiotics and Chemotherapy, 1, 309 (1951)) or on complex media such as Benett's medium (K. L. Jones, J. Bacteriol., 57, 142 (1949)). Cultures on thin plates examined under the microscope show the formation of branched filaments and of spore chains characteristic of the genus Streptomyces. The spore-bearing filaments presenting the most complex degree of development are in the form of spirals with serrated coils of several, and often more than five, turns. The spores are oval, measuring about $0.6 - 0.9$ to $0.8 - 1.2$ $\mu$.

The attachment of the spore-bearing filaments presents a verticillated structure, sometimes monoverticillated but more often biverticillated. This structure is only observable under the microscope if the spore-bearing filaments are only spirals of one or two turns or are reduced to a loop; otherwise the development of spirals is too thick and masks their attachment, hindering the observation of any secondary whorls in their structures.

Taking into account the morphological elements which show the most complex development, it can be concluded that the spore-bearing apparatus of Streptomyces 8899 and 31723 corresponds to the *Biverticillus-spira* type described in the classification of T. G. Pridham et coll. [Applied Microbiol., 6, 52 (1958)].

Since the aerial mycelium of well-developed cultures of both of the new types of Streptomyces is light blue, on comparison with Pridham's classification by series, Streptomyces 8899 and 31723 are placed in the Biverticillus-spira blue series section, in which no species are described, though *Streptomyces coeruleorubidus* appears in the Spira blue series section.

General Characteristics

On "synthetic" media, Streptomyces 8899 and 31723 generally possess a vegetative mycelium which is usually rose or orange-rose at the beginning of development, the red colour intensifying with the incubation, becoming almost bright red. On "organic" media, the vegetative mycelium is yellow-brown or red-brown. The aerial mycelium is generally well-developed on both types of medium. It is white at the beginning of its development and then very rapidly becomes a shade of light blue, called below turquoise blue. According to the degree of development or the nature of the medium, it presents a slightly variable intensity of tone, or its colour may be slightly softened. Pure red or orange-red soluble pigments are formed in synthetic media of intensity which varies with the age of the cultures; the pigment is a softened red (red-brown or rose-brown) in organic media. On Williams and McCoy medium, an abundant production of characteristic black melanic pigment is observed.

Culture Characteristics and Biochemical Properties

The culture characteristics and biochemical properties of Streptomyces 8899 and 31723 have been studied on the usual nutritive agar or liquid media used in the identification of strains of Streptomyces. The observations are given in detail in Table VII; they relate to cultures incubated at 26° C. for about 1 month. The final state of the cultures and the colours produced are given. The references or composition of the culture media are given below. The description of *S. coeruleorubidus* by G. F. Gause et coll. is given in this Table so far as possible for comparison with cultures obtained on media of similar formulae.

TABLE VII

|  | Streptomyces 8899 | Streptomyces 31723 | Streptomyces coeruleorubidus |
|---|---|---|---|
| Czapeck's agar (with sucrose) | Vegetative mycelium: slight, flat, rose, under- | Vegetative mycelium: slight, cracked, yellowish-rose, | Synthetic medium No. 1 of Grause et coll. |

TABLE VII-continued

| | Streptomyces 8899 | Streptomyces 31723 | Streptomyces coeruleorubidus |
|---|---|---|---|
| (ref. 1, medium No. 1) | side bright red. Aerial mycelium: turquoise blue. Soluble pigment: light red. | underside becoming medium red. Aerial mycelium: turquoise blue. Soluble pigment: medium red. | Vegetative mycelium: raspberry-red to grey-brown. Aerial mycelium: bluish. Soluble pigment: raspberry-red to grey-brown. |
| Czapek's agar (with glucose) (ref. 1-A) | Vegetative mycelium: slight, folded, crackled, rose, underside orange-red. Aerial mycelium: turquoise blue. Soluble pigment: red tinged with orange. | Vegetative mycelium: slight, cracked, yellowish-rose, underside becoming medium red. Aerial mycelium: turquoise blue. Soluble pigment: medium red. | |
| Agar with calcium malate (ref. 2) | Vegetative mycelium: slight, flat, underside pale rose. Aerial mycelium: turquoise blue. Soluble pigment: pale rose. Remark: complete solubilisation of calcium malate in one month. | Vegetative mycelium: slight, flat, underside pale mauve. Aerial mycelium: rather poorly developed, white to turquoise blue. Soluble pigment: rose-mauve. Remark: complete solubilisation of calcium malate in one month. | |
| Agar with tyrosine (ref. 3) | Vegetative mycelium: slight, folded, brown-black. Aerial mycelium: in traces greyish-white. Soluble pigment: dark brown. Remark: no solubilisation of the tyrosine. | Vegetative mycelium: fairly thick, folded, very dark brown. Aerial mycelium: none. Soluble pigment: dark brown. Remark: no solubilisation of the tyrosine. | |
| Agar with starch (ref. 1, medium No.10) | Vegetative mycelium: thick, little folded, yellowish-rose, underside pale rose mauve. Aerial mycelium: turquoise blue. Soluble pigment: rose tinged with orange. | Vegetative mycelium: thick, finely folded underside dull red. Aerial mycelium: turquoise blue. Soluble pigment: rose tinged with orange. | Vegetative mycelium: colourless or rose. Aerial mycelium: whitish-bluish. Soluble pigment: none. No hydrolysis or slow hydrolysis of the starch. |
| Agar with glucose (ref. 1, medium No. 7) | Vegetative mycelium: finely folded, fluted, underside light yellowish-brown. Aerial mycelium: poorly developed, white to turquoise blue. Soluble pigment: yellow-brown to light red-brown. | Vegetative mycelium: slight and very finely folded, yellowish-red then reddish-brown. Aerial mycelium: traces, white. Soluble pigment: light yellowish-brown. | (Organic medium No. 2 of Gause et coll.) Vegetative mycelium: reddish-brown. Aerial mycelium: sparse, whitish. Soluble pigment: reddish-brown. |
| Asparagine-glycerine agar (ref. 1, medium No.3) | Vegetative mycelium: slight, little folded, pale rose tinged with orange, underside rose tinged with orange. Aerial mycelium: turquoise blue. Soluble pigment: pale rose tinged with orange | Vegetative mycelium: fairly thick and folded, light rose, underside red tinged with orange. Aerial mycelium: turquoise blue. Soluble pigment: pale rose tinged with orange. | |
| Benett's agar (ref. 4) | Vegetative mycelium: fairly thick, finely folded, light red-brown, underside dark brown. Aerial mycelium: turquoise blue. Soluble pigment: red-brown | Vegetative mycelium: slight and very finely folded, shrimp-red, underside reddish-brown. Aerial mycelium: turquoise blue. Soluble pigment: weak, rose-brown. | |
| Starch-ammonium phosphate agar (ref. 5) | Vegetative mycelium: slight, flat, underside pale yellowish to nearly blue. Aerial mycelium: very well developed, turquoise blue. Soluble pigment: none. | Vegetative mycelium: slight, flat, colourless, underside slightly rose tinted. Aerial mycelium: very well developed, turquoise blue. Soluble pigment: none. | |
| Maltose-tryptone agar (ref. 6) | Vegetative mycelium: very thick, folded, crackled, underside black-brown. Aerial mycelium: very well developed, turquoise blue to grey blue. Soluble pigment: melanic pigment, intense black-brown, characteristic. | Vegetative mycelium: thick, folded, crackled, underside black-brown. Aerial mycelium: very well developed, turquoise blue to grey blue. Soluble pigment: melanic pigment, intense black-brown, characteristic. | |
| Gelatin (stab culture) (7) | Vegetative mycelium: slight pellicle with yellowish underside. Aerial mycelium: poorly developed, remaining white. Soluble pigment: medium brown. Remark: slow and incomplete liquefaction of the gelatine. | Vegetative mycelium: pellicle fragmented with yellowish-rose underside. Aerial mycelium: poorly developed, white. Soluble pigment: yellow-brown, not abundant. Remark: slow and incomplete liquefaction of the gelatine. | Vegetative mycelium: dark yellow or grey-brown. Soluble pigment: grey-brown. Remark: slow and complete liquefaction of the gelatine. |
| Potato (ref. 1, medium No.27) | Vegetative mycelium: thick, finely folded, light yellow-brown then reddish-brown. Aerial mycelium: turquoise blue. | Vegetative mycelium: thick and folded, red tinged with orange to reddish brown. Aerial mycelium: turquoise blue. | Vegetative mycelium: smooth, colourless, yellowish or dark rose. Aerial mycelium: white-blue, blue or green-blue; some |

TABLE VII-continued

| | Streptomyces 8899 | Streptomyces 31723 | Streptomyces coeruleorubidus |
|---|---|---|---|
| | Soluble pigment: dark: red-brown. | Soluble pigment: dark red-brown. | strains rose-blue.<br>Soluble pigment: sometimes dark rose. dark rose. |
| Skimmed milk (ref. 8) | Vegetative mycelium: thick, dark yellowish-brown ring. | Vegetative mycelium: slight yellowish-rose to reddish-brown ring. | Vegetative mycelium: colourless or yellowish |
| | Aerial mycelium: traces, white. | Aerial mycelium: traces, white. | Soluble pigment: grey-brown. |
| | Soluble pigment: brown.<br>Remarks: neither coagulation nor peptonisation, change in ph very slight, from 6.3–6.5 to 6.0–6.3. | Soluble pigment: brown.<br>Remarks: neither coagulation nor peptonisation, weak acidification of medium as with S. 8899. | Remarks: coagulation and peptonisation negative or positive according to strain. |
| Strarch solution (ref. 1, medium No.19) | Vegetative mycelium: slight pellicle, bright red. | Vegetative mycelium: slight pellicle, bright red. | |
| | Aerial mycelium: poorly developed, white to turquoise blue. | Aerial mycelium: traces, white. | |
| | Soluble pigment: red tinged with orange. | Soluble pigment: red tinged with orange. | |
| | Remark: hydrolysis of the starch complete in one month. | Remark: hydrolysis of the starch complete in one month. | |
| Synthetic solution with nitrate (ref. 7) | Vegetative mycelium: poorly developed, slight colourless pellicle. | Vegetative mycelium: several isolated, yellowish colonies. | Vegetative mycelium: colourless. |
| | Aerial mycelium: none.<br>Soluble pigment: none.<br>Remark: no reduction to nitrite. | Aerial mycelium: none.<br>Soluble pigment: none.<br>Remark: no reduction to nitrite. | Soluble pigment: sometimes yellow.<br>Remarks: reduction positive or negative according to strain. |
| Microscopic morphology medium: refs. 4 and 5. | Spore-bearing filaments in the form of spirals arranged in a secondary verticillate structure. Spores short ovals. | As Streptomyces 8899. | Spirals of 5–7 turns. spherical spores. |

| | Reference or Compositions of Culture Media |
|---|---|
| (1) | S. A. Waksman; "The Actinomycetes," Chronica Botanica Company, Waltham (Mass.), U.S.A., 1950, pages 193–197. |
| (1-A) | Obtained by replacing sucrose by the same weight of glucose in the preceeding formula. |
| (2) | Calcium malate 1%, ammonium chloride 0.05%, dipotassium phosphate 0.05%, agar 2%. |
| (3) | reptone 0.5%, meat extract 0.3%, tyrosine 0.5%, agar 2%. |
| (4) | K. L. Jones, J.Bacteriology, 57, 142 (1949). |
| (5) | Grundy et coll., Antibiotics and Chemotherapy, 1, 309 (1951). |
| (6) | A. M. Williams and E. McCoy, Appl. Microbiol., 1, 307 (1953). |
| (7) | Manual of Methods for pure culture study of bacteria, Society of American bacteriologists (II 50 – 18). |
| (8) | Commercial skimmed milk powder, reconstituted according to the manufacturers' instructions. |

Utilisation of Various Hydrocarbon Substances

[According to the method of T. G. Pridham and D. Gottlieb, J. Bact. 56, 467 (1946)]

The cultures are carried out on agar slopes at 26° C. Amongst substances regularly giving rise to a rapid and complete growth are: xylose, arabinose, rhamnose, glucose, galactose, mannose, lactose, maltose, raffinose, dextrin, starch, glycerol (in S. 8899 only), adonitol, mannitol, sorbitol, inositol (in S. 8899 only). In contrast, sorbose, inulin (in S. 31723 only), esculin, erythritol and dulcitol allow no development, or only very restricted development. Finally, substances which produce an irregular, moderate or weak growth in the experiments include ribose, levulose, sucrose, inulin (in S. 8899 only), glycerol (in S. 31723 only), and inositol (in S. 31723 only).

Systematic Classification

The characteristics to be taken into consideration for the systematic classification of S. coeruleorubidus strains 8899 and 31723 are: the turquoise blue colour of the aerial mycelium; the biverticillate structure of the spirals of the spore-bearing apparatus; the positive melamine reaction of cultures on appropriate media; the particular red colour of the vegetative mycelium on appropriate media; and the particular red colour of soluble pigments on appropriate media.

The first two characteristics place S. coeruleorubidus strains 8899 and 31723 in the biverticillus-spira blue series section of Pridham's classification, in which no other species is described. The properties taken together place S. coeruleorubidus strains 8899 and 31723, in the new classification of S. A. Waksman "The Actinomycetes" (The Williams and Wilkins Company, Baltimore, 1961), Vol. II, page 155, in the melamine + group, series 5 (red to reddish-orange growth); no species occurs in this series having a blue aerial mycelium. S. coeruleorubidus strains 8899 and 31723 may therefore by placed in this series with the qualification "blue aerial mycelium".

The process of the invention for the production of antibiotic 9865 RP comprises cultivating Streptomyces 8899 or Streptomyces 31723 or a productive mutant thereof in a nutrient medium containing assimilable sources of carbon, nitrogen, and mineral salts until substantial antibiotic activity is produced by the said microorganism in the said medium, and recovering the said antibiotic from the medium. The culture of Streptomyces 8899 or Streptomyces 31723 may be carried out by any method of aerobic surface or submerged culture, but the latter is preferred for reasons of convenience. For this purpose the various types of apparatus currently used in the fermentation industry are employed.

The following scheme for making a production culture is preferably used:

The fermentation medium must contain assimilable sources of carbon, nitrogen, and mineral salts and, optionally, growth factors, all these elements being introduced in the form of well-defined substances or as complex mixtures, such as those encountered in biological products of various origins.

Carbohydrates, such as glucose, lactose, sucrose, molasses, dextrins, starch, and other carbohydrates such as the sugar alcohols, e.g. mannitol, may be used as carbon sources, and also certain organic acids, e.g. lactic, citric, and tartaric acids. Certain animal or vegetable oils such as lard or soya oil may advantageously replace these various carbon sources, or be combined with them. A wide range of sources of assimilable nitrogen are suitable. They may be simple chemical substances such as nitrates, inorganic and organic ammonium salts, urea and amino acids. They may also be complex substances containing nitrogen principally in the form of protein, such as casein, lactalbumin, gluten and hydrolysates thereof, soya-, groundnut-, and fish-meals, meat extracts, yeast, distillers' solubles and corn-steep. Amongst the mineral elements added, certain may exert a buffering or neutralising effect, such as alkali metal or alkaline earth metal phosphates and calcium and magnesium carbonates. Other mineral salts contribute to the ionic equilibrium necessary for the development of Streptomyces 8899 and 31723 and the formation of the antibiotic, for example alkali metal and alkaline earth metal chlorides and sulphates. In addition, certain substances act as activators of the metabolic reactions of Streptomyces 8899 and 31723; these are the salts of zinc, cobalt, iron, copper and manganese.

The pH of the nutrient medium at the beginning of culture should be between 6.0 and 7.8, and preferably 6.5 to 7.5. The optimal temperature for the culture is 25°–28° C., but satisfactory production is obtained at temperatures between 23° and 35° C. The aeration of the fermentation medium may be varied over a fairly wide range of values but it has been found that aeration rates of 0.3 to 2 liters of air per minute per liter of medium are particularly suitable. The maximal yield of antibiotic is obtained after 2 to 5 days of culture, this period depending essentially on the medium used. From the foregoing it will be appreciated that the general conditions for the culture of Streptomyces 8899 and 31723 for the production of antibiotic 9865 RP may be varied to a fairly wide degree.

9865 RP may be isolated from the fermentation cultures by various methods. The fermentation culture may be filtered at a pH between 1.5 and 9 and, in these conditions, the major part of the active material passes into the filtrate. After washing with water, the filter-cake retains practically no active material. It is advantageous to carry out this operation using an acid medium, and particularly one acidified with oxalic acid to a pH between 1.5 and 2. It is also possible to carry out the filtration at a pH between 2 and 7, preferably near to 2, in the presence of an aliphatic alcohol containing 1 to 3 carbon atoms.

In these extraction operations 9865 RP is obtained in aqueous or aqueous-alcoholic solution and it is then extracted with a water-immiscible organic solvent such as butanol, methyl isobutyl ketone, ethyl acetate or chloroform, at a pH between 5.5 and 9, preferably about 7.5. This extraction may be preceded by absorption of the antibiotic on an ion-exchange resin, in which case the aqueous solution is adjusted to a pH about 4 and then treated with a cationic carboxylic exchange resin, preferably Amberlite IRC 50, in the hydrogen form. Elution is then effected with a saline or acidic, aqueous-alcoholic soluton, preferably with methanol containing 10% water and 1% sodium chloride. The eluate is concentrated to remove the alcohol and then extracted as described above.

The fermentation medium may also be directly extracted with a water-immiscible organic solvent such as butanol, ethyl acetate or chloroform, at a pH between 5.5 and 9, preferably about 7.5. In this case, all the active material passes into the organic phase, which is separated from the aqueous phase by the usual methods.

Whatever the mode of extraction chosen, the antibiotic 9865 RP is finally obtained in organic solution. It may be advantageous at this stage to purify the antibiotic by successively passing it into aqueous solution and into organic solution by varying the pH. The crude antibiotic may then be isolated from the organic solution obtained in the last-mentioned operation by concentration or precipitation with a poor solvent for the antibiotic, such as hexane. A method of isolation which has been found to be particularly advantageous consists of acidifying the organic solution to a pH of about 4, preferably with acetic acid, and concentrating it under reduced pressure to a smaller volume. Addition of a poor solvent for 9865 RP, such as hexane, to the concentrate obtained causes the precipitation of the crude antibiotic.

To obtain 9865 RP in a purer state, all the usual methods may be used, such as chromatography on an adsorbent substances, countercurrent distribution, or partition between various solvents. It has been found particularly advantageous to utilise one of the following two methods: chromatography on alumina at pH 4 of the crude antibiotic dissolved in butanol; and solution of the crude antibiotic in a mixture of methylene chloride-carbon tetrachloride-water (5:1:6 by volume), decantation of the aqueous phase followed by its extraction with methylene chloride, combination of the methylene chloride extracts, and concentration of the latter under reduced pressure, followed by the addition of hexane to the concentrate obtained to precipitate the purified antibiotic. A similar method may also be used in which the methylene chloride is replaced by ethyl acetate.

It is possible to repeat the different methods indicated for the extraction and isolation of 9865 RP several times according to manufacturing requirements, to obtain this antibiotic in a form pure enough for the purposes envisaged.

The 9865 RP isolated by any of the foregoing methods may then be separated into its three constituents, 13057 RP daunorubicin, 13213 RP and 13330 RP. This separation may be effected by the usual methods used for the separation of an antibiotic into its constituents, such as chromatography on various substances or countercurrent distribution. It has been found that the latter gives the more advantageous results, in particular when carried out by one of the following processes, which are, however, only preferred procedures: to obtain 13057 RP daunorubicin alone, countercurrent distribution of 9865 RP with a butanol-phosphate-buffer of pH 7-7.5 system; to obtain 13213 RP alone, countercurrent distribution of 9865 RP in a butanol-ethyl acetate system buffered to pH 4; and to obtain the separation of the three constituents from 9865 RP, two successive countercurrent distributions, at first with a limited number of transfers with a system composed of two chlorinated aliphatic hydrocarbons buffered to pH 5.8, which produces two fractions, an aqueous phase containing 13057 RP daunorubicin contaminated with 13213 RP and an organic phase containing a mixture of 13213 RP and 13330 RP contaminated with 13057 RP daunorubicin, followed by the separate treatment of the two fractions thus obtained with an ethyl acetate-methanol system phosphate-buffered to pH 5.5, which permits, on the one hand, the isolation of 13057 RP daunorubicin and, on the other, the separation of 13213 RP and 13330 RP.

The various countercurrent distribution operations may be preceded or followed by the usual purification processes, particularly extraction or recrystallisation, in order to obtain the three constituents in a form pure enough for the use envisaged.

The following non-limitative Examples illustrate the invention. Activity is throughout determined by turbidimetric estimation, using *Klebsiella pneumoniae* as the sensitive organism, by comparison with a sample of 9865 RP of known activity used as control. This activity is expressed in units (u) per mg. for solid products and in units per cc. for solutions. (The unit is defined as the smallest quantity of product which, dissolved in 1 cc. of an appropriate medium, inhibits the growth of *Klebsiella pneumoniae* under the conditions in question).

EXAMPLE 1

A 170 liter fermentation vessel is charged with:

| | |
|---|---|
| Corn steep | 2.400 kg. |
| Sucrose | 3.600 kg. |
| Calcium carbonate | 0.900 kg. |
| Ammonium sulphate | 0.240 kg. |
| Water to | 100 liter. |

This culture medium has a pH of 6.15. It is sterilised by passage of steam at 122° C. for 40 minutes. After cooling, the volume of the broth is 120 litres and the pH is 7.20. The medium is then seeded with 200 cc. of a culture in an agitated Erlenmeyer flask of the strain Streptomyces 31723. The culture is carried out for 27 hours at 26°–27° C. with agitation and aeration with sterile air. It is then suitable for seeding the production culture.

The production culture is carried out in an 800 litre fermentation vessel charged with the following:

| | |
|---|---|
| Soya flour | 20 kg. |
| Distillers' solubles | 2.500 kg. |
| Starch | 10 kg. |
| Soya oil | 2.500 liters |
| Sodium chloride | 5 kg. |
| Water to | 465 liters. |

The pH of the medium thus obtained is adjusted to 7.20 with concentrated sodium hydroxide solution (400 cc.). The medium is then sterilised by the passage of steam at 122° C. for 40 minutes. After cooling, the volume of the broth is 500 liters and the pH is 6.75. It is then seeded with 50 liters of the culture from the 170 liter fermentation vessel. Culture is carried out at 28° C. for 67 hours with agitation and aeration with sterile air. The pH of the medium is then 7.40 and the volume of the fermentation culture is 520 liters. The quantity of antibiotic present in the medium is 29 u/cc.

EXAMPLE 2

An inoculum culture is carried out in a 170 litre fermentation vessel under the same conditions as in Example 1 but seeding with 200 cc. of a culture in an agitated Erlenmeyer flask of the strain Streptomyces 8899.

The production culture is then carried out in an 800 litre fermentation vessel charged with the medium described in Example 1. The pH of the medium is adjusted to 8.10 with concentrated sodium hydroxide solution (750 cc.), and the medium is then sterilised by the passage of steam at 122° C. for 40 minutes. After cooling, the volume of the broth is 500 litres and the pH 6.80. The medium is then seeded with 75 liters of the culture in the 170 litre fermentation vessel, and the culture is carried out at 26°–27° C. for 67 hours with agitation and aeration with sterile air. The pH of the medium is then 7.40 and the volume of the fermentation culture is 545 liters. The quantity of antibiotic present in the medium is 9.1 u/cc.

EXAMPLE 3

The fermentation culture from Example 1 (520 liters: activity 29 u/cc.) is placed in a vessel equipped with an agitator and the pH is adjusted to 1.8 with a concentrated solution of oxalic acid. Agitation is carried out for 1 hour and a filtration adjuvant (20 kg.) then added. The mixture is filtered on a filter-press and the filter-cake washed with water (100 liters) acidified to pH 2 with oxalic acid. The filtrate (612 liters) is treated with concentrated sodium hydroxide solution until the pH is 4.5. The filtrate is then passed through a column containing Amberlite IRC 50 in hydrogen form (20 liters: diameter of column 15.2 cm., height of column 200 cm., height of resin at rest in column 110 cm.). The filtrate passes through the bed of Amberlite from base to top at a rate of 40 liters/hour. The column is then washed with water (100 liters) at a rate of 50 liters/hour circulating from base to top and then with methanol (containing 10% water; 75 liters) circulating from top to base at a rate of 50 liters/hour. The washings are discarded and the column is then eluted with a solution having the following composition (per liter):

| | |
|---|---|
| sodium chloride | 10 g. |
| water | 100 cc. |
| methanol to | 1000 cc |

The eluate (100 litres), which contains the major part of the antibiotic, is concentrated under reduced pressure at 35° C. to 10 litres. The concentrate is extracted at pH 7.5 with chloroform (2 × 5 litres). The chloroformic extract is adjusted to pH 4 with a solution of acetic acid in chloroform (10:100 by volume) and then concentrated at 30° C. under reduced pressure to 100 cc. The antibiotic is precipitated by the addition of hexane (1 litre), separated, washed and dried to give an amorphous red powder (9 g.) of activity 1,400 u/mg.

EXAMPLE 4

The crude antibiotic (17.1 g.) obtained as described in Example 3 (activity 1530 u/mg.) is dissolved with stirring in a mixture of methylene chloride (1.5 liters), carbon tetrachloride (0.3 liters) and water (1.8 litres). The pH is then adjusted to 3 by the addition of normal hydrochloric acid (8 cc.). After decanting, the aqueous phase is treated with methylene chloride (7 litres) and 0.1N sodium hydroxide solution (200 cc.) to give a pH of 7.5. After decanting, the aqueous phase is again extracted at pH 7.5 with methylene chloride (3.5 litres). The methylene chloride extracts are combined and concentrated to 100 cc. After the addition of hexane (1 liter) to the concentrate, a product precipitates which is filtered off, washed and dried at 30° C. under reduced pressure to give the antibiotic 9865 RP (9.15 g.) in the form of an amorphous orange-red powder of activity 2180 $\mu$/mg.

EXAMPLE 5

A mixture is prepared of methylene chloride, carbon tetrachloride and MacIlvaine buffer — pH 5.8 (20 cc. of this buffer are prepared by the addition of 12.09 cc. of 0.2 M $Na_2HPO_4$ solution of 7.91 cc. of 0.1 M citric acid solution) in the proportions 2:1:3 (by volume). When this mixture is in equilibrium, the two phases are separated. 9865 RP (10 g. of activity 1750 $\mu$/mg. (obtained as described in Example 4) is dissolved in a mixture of the phases (1 liter of each). This system is subjected to a countercurrent distribution of 6 transfers in 5 liter cells, using the heavy (organic solvent) phase as the mobile phase and the light (aqueous) phase as the stationary phase and using 1 liter of each phase each time. The mixtures of lower phases (mixture A) and upper phases (mixture B) of the first 4 cells, and the mixtures of lower phases (mixture C) and upper phases (mixture D) of the last 3 cells, are collected separately.

Mixture B is adjusted to pH 7.5 by the addition of normal sodium hydroxide solution (300 cc.) and then extracted with chloroform (4 litres, 2 liters and 1 liter). The chloroformic extracts and mixture A are combined and concentrated under reduced pressure (to 700 cc.). The concentrate is washed with water at pH 7.5 (2 × 350 cc.) and the mother liquors of the washings are extracted with chloroform (2 × 100 cc.). The washed concentrate and the chloroformic extracts are combined and concentrated under reduced pressure to 70 cc. Hexane (700 cc.) is then added and the precipitate produced is filtered off, washed and dried under reduced pressure at 30° C., giving a fraction $F_1$ (5.1 g.) containing principally the antibiotic 13057 RP daunorubicin.

In a separate operation, mixture D is extracted with methylene chloride (3 liters and 1.5 litres). The methylene chloride extracts and mixture C are combined and concentrated under reduced pressure to 800 cc. The concentrate is washed with water (400 cc.) and then concentrated again to 700 cc. Hexane (1 litre) is added and the precipitate produced is filtered off, washed and dried under reduced pressure at 30° C., to give a fraction $F_2$ (3.7 g.) containing principally 13213 RP and 13330 RP.

EXAMPLE 6

A product (10 g.), similar to fraction $F_1$ mentioned above, is subjected, after being dissolved in an ethyl acetate-methanol — pH 5.5 M/15 phosphate buffer system (8:3:5 by volume; 200 cc.), to a countercurrent distribution of 110 transfers in a 50 cell Craig apparatus (50 transfers in the apparatus and 60 transfers by the "single withdrawal" technique) beginning at the first two cells. The mixture of the upper phases of cells 0 to 37 (3.8 liters) is recovered and concentrated to 300 cc.) The concentrate thus obtained and the mixture of the lower phases of cells 0 to 37 (3.8 liters) are then combined and concentrated to 800 cc. The pH is adjusted to 8 by the addition of normal sodium hydroxide solution (180 cc.) and the solution obtained is extracted with chloroform (800 cc. and 400 cc.). The chloroformic extracts are concentrated to 400 cc. and washed with water (400 cc.) made alkaline to pH 8. The mother liquors of the washing are extracted with chloroform (200 cc.). The washed concentrate and the chloroformic extracts are combined, concentrated to 400 cc., washed with water (400 cc.) made alkaline to pH 8, and concentrated to 100 cc. Butanol (200 cc.) is added, and the mixture concentrated to 100 cc. The butanolic solution obtained is adjusted to pH 3.5 by the addition of butanol saturated with normal hydrochloric acid (30 cc.) and kept for 12 hours at 4° C. Crystals form which are filtered off, washed and dried, giving a first crop (4.55 g.) of crude 13057 RP daunorubicin hydrochloride. Concentration to 100 cc. of the crystallisation mother liquors, addition of hexane (1 litre) and filtering, washing and drying the precipitate produced, gives a second crop (2.5 g.) of crude 13057 RP daunorubicin hydrochloride.

EXAMPLE 7

Crude 13057 RP daunorubicin hydrochloride (3.75 g.), obtained as described in Example 6, is dissolved in dioxan (40 cc.) containing 20% water. The solution obtained is filtered and anhydrous dioxan (15 cc.) is added over 2 hours, followed by anhydrous dioxan (235 cc.) over 30 minutes. A product crystallises which is separated, washed and dried, giving 13057 RP daunorubicin hydrochloride (2.75 g.) in the form of orange-red needles, m.p. 225°–230° C. (with decomposition), of activity 151 u/mg.

This compound (0.208 g.) is dissolved in a mixture of water (200 cc.) and butanol (150 cc.). 0.1N sodium hydroxide solution (3.4 cc.) is added, the mixture is separated and the aqueous phase then extracted with butanol (50 cc.). The butanolic extracts are combined, washed with water made alkaline to pH 8 (2 × 100 cc.) and concentrated to 10 cc. The concentrate obtained is treated with hexane (50 cc.) and the precipitate produced is filtered off, washed and dried, giving 13057 RP daunorubicin (0.0945 g.) in the form of an amorphous red powder, activity 160 μ/mg.

EXAMPLE 8

A product (5 g.), similar to fraction $F_2$ obtained in Example 5, is subjected, after being dissolved in an ethyl acetate-methanol — pH 5.5 M/15 phosphate buffer system (8:3:5 by volume; 200 cc.), to a countercurrent distribution identical with that described in Example 6. The mixture of the upper phases of cells 36 to 89 (5.3 litres) is recovered and concentrated to 500 cc. The concentrate thus obtained and the mixture of the lower phases of cells 36 to 89 (5.3 liters) are combined and concentrated to 800 cc. The concentrate is extracted successively with methylene chloride 2 × 800 cc.) and chloroform (800 cc.). The extracts obtained are combined, concentrated to 400 cc., washed with water at pH 7.5 (2 × 400 cc.) and then concentrated to 10 cc. Addition of hexane (100 cc.) causes the precipitation of a product which is filtered off, washed and dried under reduced pressure, giving 13213 RP (1.1 g.) in the form of an amorphous orange-red powder, activity 2,650 μ/mg.

EXAMPLE 9

The fermentation culture (500 litres) obtained in Example 2 is treated as described in Example 3, giving crude 9865 RP (8.5 g.), activity 395 μ/mg. This crude product (17 g.) is purified as described in Example 4 but replacing the methylene chloride by ethyl acetate to give 9865 RP (3 g.), activity 1300 μ/mg.

EXAMPLE 10

9865 RP (12.4 g.), obtained as described in Example 9, is subjected, in a butanol — pH 7.35 M/3 phosphate buffer system, to a 50-transfer countercurrent distribution. By extraction with butanol of the lower phases of cells 12 to 35, concentration of the butanolic extracts, washing and the addition of hexane, a first crop (1 g.) of 13057 RP daunorubicin hydrochloride is obtained, followed, after concentration of the mother liquors, by a second crop (1.1 g.) of the same product. These two crops, after recrystallisation from aqueous dioxan, take the form of orange-red needles, m.p. about 225°–230° C. (with decomposition), activity 67 μ/mg.

A similar treatment applied to cells 36 to 49 gives crude 13213 RP (1.1 g.), activity 1800 μ/mg., which, after being subjected to a 50-transfer countercurrent distribution in a butanol-ethyl acetate pH 4 MacIlvaine buffer system (3:7:10 by volume), gives 13213 RP (0.5 g.) in the form of an amorphous orange-red powder, activity 2000 μ/mg.

EXAMPLE 11

A fermentation culture (625 liters), prepared as described in Example 2, is placed in an agitated vessel. The pH is adjusted to 9 with concentrated sodium hydroxide solution. Agitation is continued for 30 minutes and a filter-adjuvant (32 kg.) then added. The mixture is filtered on a filter-press and washed with water (275 liters). The filtrate (780 liters) is treated with sodium chloride (156 kg.) and the pH adjusted to 3 with 12N hydrochloric acid. The filtrate is then extracted with butanol (260 liters) and the butanolic extract concentrated under reduced pressure at 35° C. to 4 liters. The concentrate is filtered and the crude antibiotic precipitated from the clarified solution with petroleum ether (32 liters), separated, washed and dried in vacuo at 30° C., giving crude 9865 RP (227 g.) as a red-brown powder, activity 45 μ/mg.

The crude product (50 g.) obtained is dissolved in butanol saturated with water (200 cc.) and the solution obtained is chromatographed at pH 4 through a column containing alumina (500 cc.). After fixation of the antibiotic, the chromatogram is developed and eluted with butanol saturated with water (4 liters). Three coloured fractions are recovered (respective volumes 450 cc., 1500 cc. and 1500 cc.). The first fraction is concentrated under reduced pressure to 50 cc. and then treated with hexane (500 cc.), giving 9865 RP (8.3 g.), activity 68.5 μ/mg. The second two fractions are each concentrated under reduced pressure to 100 cc. and treated with hexane (1 liter each) to give, respectively, 9865 RP (4.4 g.), activity 216 μ/mg. and 9865 RP (1.35 g.), activity 800 μ/mg.

EXAMPLE 12

A fermentation culture (425 liters), prepared as described in Example 1 (activity 40 u/cc.), is acidified to pH 1.8 with oxalic acid and filtered. The filter-cake is washed with water (100 liters) acidified to pH 2 with oxalic acid and the combined filtrate obtained (500 liters) is extracted at pH 8 with chloroform (150 liters and 100 liters). The extracts are combined and extracted with water at pH 4 (80 liters and 50 liters). The aqueous extract obtained is made alkaline to pH 8 with normal sodium hydroxide solution and extracted with chloroform (40 litres and 20 liters). The chloroformic extracts thus obtained are acidified to pH 4 with a solution of acetic acid in chloroform (10:100 by volume) and the acidified extract concentrated at 30° C. under reduced pressure to 50 cc. The crude antibiotic is then precipitated by the addition of hexane (500 cc.), separated, washed and dried in vacuo at 30° C., giving 9865 RP (680 mg.) in the form of a red powder, activity 1080 μ/mg.

EXAMPLE 13

9865 RP (500 mg.), obtained as described in Example 4, is dissolved in normal sulphuric acid (100 cc.) and the solution obtained is heated for 20 minutes on a water-bath. After cooling and extracting ethyl acetate (3 × 200 cc.), the organic extract is dried over anhydrous sodium sulphate, filtered and concentrated to a small volume, giving, after filtering, washing and drying, crystals (218.5 mg.). These crystals (150 mg.) are dissolved in chloroform (3 cc.) and benzene (1.5 cc.) and the solution obtained is chromatographed on 20 sheets of Arches No. 310 paper impregnated with a solution of acetone containing 20% formamide, and developed for 90 minutes by means of a 2:1 mixture of chloroform and benzene saturated with formamide. The principal zone of Rf = 0.86 is cut out of each of the 20 sheets and the 20 zones thus cut out are comminuted in a mixer in the presence of methanol. The mixture obtained is filtered, concentrated, and water (10 volumes) added. The precipitate obtained is filtered off, washed and dried under reduced pressure to give crystals (120 mg.). These crystals (170 mg.) are dissolved in dioxan containing 20% water (15 cc.) and water acidified to pH 4 with 0.1N hydrochloric acid is added dropwise. The crystals formed are filtered off, washed and dried, thus giving the aglycone of 9865 RP (130 mg.) in the form of orange-red needles, having a first melting point at 160° C. and a second at 225°–230° C.

EXAMPLE 14

13057 RP daunorubicin (500 mg.), obtained as described in Example 7, is treated with sulphuric acid as described in Example 13 for 9865 RP, giving crystals (300 mg.) which, after being treated as described in Example 13, yield the aglycone of 13057 RP daunorubicin (202 mg.) in the form of orange-red needles having a first melting point at 160° C. and a second at 225°–230° C. This aglycone is identical with that of 9865 RP.

The present invention includes within its scope pharmaceutical compositions containing at least one of the antibiotics defined above is association with a compatible pharmacologically acceptable carrier. The compositions may also contain other physiologically active substances. These compositions may be made up in any pharmaceutical form appropriate for the route of administration in question. Intravenous administration of 13057 RP daunorubicin is preferred.

Solid compositions for oral administration include compressed tablets, pills, dispersible powders, and granules. In such solid compositions one or more of the new anitbiotics is, or are, admixed with at least one inert diluent such as calcium carbonate, potato starch, alginic acid, or lactose. The compositions may also comprise, as is normal practice, additional substances other than inert diluents, e.g. lubricating agents, such as magnesium stearate. Liquid compositions for oral administration include pharmaceutically acceptable emulsions, solutions, suspensions, syrups and elixirs containing inert diluents commonly used in the art, such as water and liquid paraffin. Besides inert diluents such compositions may also comprise adjuvants, such as wetting and suspending agents, and sweetening, flavouring, perfuming and preserving agents. The compositions according to the invention, for oral administration, also include capsules of absorbable material such as gelatin containing one or more of the new antibiotics with or without the addition of diluents or excipients.

Preparations according to the invention for parenteral administration include sterile aqueous or nonaqueous solutions, suspensions, or emulsions. Examples of non-aqueous solvents or suspending media are propylene glycol, polyethylene glycol, vegetable oils such as olive oil, and injectable organic esters such as ethyl oleate. These compositions may also contain adjuvants such as preserving, wetting, emulsifying and dispensing agents. They may be sterilised by, for example, filtration through a bacteria-retaining filter, by incorporation in the compositions of sterilising agents, by irradiation, or by heating. They may also be manufactured in the form of sterile solid compositions, which can be dissolved in sterile water or some other sterile injectable medium immediately before use.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.001% by weight of active substance when required for administration by injection. For oral administration the preparations will normally contain at least 0.1% by weight of active substance.

For the treatment of human cancer by intravenous administration, daily doses are generally between 0.1 and 2 mg /kg for an adult. Compositions for injection consist, for example, of a solution containing 0.1 mg/cc. of active substance in sterile physiological saline.

In more detail, the manner of using 13057 RP daunorubicin in the treatment of various types of cancer is as follows:

Daunorubicin is essentially intended to obtain a remission. The induction treatment, and the reinduction treatments which may follow it, consist of injections repeated at progressively increasing intervals, spaced over from one to several months, which excludes the use of daunorubicin as a maintenance treatment by itself and for a prolonged period. Daunorubicin exercises a depressant action on the blood-forming centers and its administration is sometimes accompanied by cardiac complications. Daunorubicin cannot be used without frequent and regular blood tests and rigorous cardiological testing, before and during treatment.

Daunorubicin is preferably administered by means of intravenous perfusion. Solutions of daunorubicin must be prepared at the time they are required. This is done, for example, by shaking together in a stoppered vessel 20 mg of dry daunorubicin and the contents of an ampoule (4 cc) of solvent (water for injectable preparations), until the daunorubicin is completely dissolved. The solution prepared in this manner is injected through a catheter as a venous perfusion in 100 or 200 cc of isotonic sodium chloride solution. In order to avoid irritation by the medication of the surrounding tissues and of the vascular linings, it is essential that administration should be strictly intravenous and that the rate of perfusion should be rapid so as to prevent local stasis of the product.

The dosage varies according to the clinical circumstances, the therapeutic response, and the blood picture. Also, the data given hereafter indicate mainly an order of magnitude.

Treatment of acute leukaemias must be intensive and of short duration; depending on the case, it comprises one or more courses. In the lymphoblastic forms of leukaemia, the actual trend is to administer a daily dose of 1 mg/kg body weight for two to eight consecutive days, and to cease injections when the leucopenia reaches 1,000 to 1,500 units per $mm^3$. It will be recalled that characteristic changes in the medullary cytology facilitate the conducting of the treatment and help in its adaptation to each particular case. The appearance of giant lymphoblasts slightly preceding aplasia, indicates that administration of daunorubicin should be suspended. It is, moreover, at the end of the aplastic phase, when the number of leucocytes is rising again, that adjustement of the therapeutic dose is difficult. When, the day after medication was stopped the leucopenia worsens and the medullary blasts change, it is required to wait for regeneration of the blood before proceeding with a bone marrow test. If the leucopenia is not accentuated and the medullary cytology remains high with persistence of blastic cells, a second course is undertaken. When the marrow is poor and blastic, one or two complementary injections at intervals of 1 or 2 days are frequently necessary. The overall dosage corresponding to the group of courses making up the initial treatment, such as has just been defined, is far from being uniform; calculated per kg weight, it sometimes reaches 20 mg, a dose of around 25 mg being considered a mean safe dose. The procedure is identical in acute myeloblastic leukaemias, but the daily dose is increased to 2 mg/kg.

It is also possible to adopt, for the treatment of acute leukaemias in their evolutive stage, a dosage based on the body surface area, and to use a daily dose of 30 mg/sq. meter for 3 to 5 successive days depending on the tolerance. After a minimum lapse of five days, a new course of the same duration is carried out; a total of three courses may be undertaken. It is emphasised that the overall dose could not be predicted; it varied in the course of experiments from 100 mg to 350 mg/sq. meter.

In chronic myeloid leukaemias, administration of 2 mg/kg of daunorubicin every 2 or 3 days, with twice-weekly testing of the leukocytosis, has been proposed. The dosage seems to be 1 mg/kg, 2 or 3 times a week, in Hodgkin's disease and various solid tumours, with a screening haemogram before each injection.

Various schemes of multiple chemotherapy incorporating daunorubicin have been proposed. One such technique involves an initial treatment completed by a reinforcing therapy on which reinduction treatments are grafted. The initial treatment combines daily oral administration of prednisone and weekly intravenous injections, in the form of a perfusion, of daunorubicin and vincristine until complete remission is obtained. Calculated per square metre of body surface, the doses are 100 mg per day of prednisone, 2 mg of vincristine and 60 mg of daunorubicin per week. Fifteen days after remission, a repeat injection of vincristine (2 mg/m$^2$) and daunorubicin (30 mg/m$^2$) is given; then the maintenance treatment is started, combining daily ingestion of 6-mercaptopurine (90 mg/m$^2$) and intramuscular administration, every 7 days, of methotrexate (15 mg/m$^2$). The reinduction treatments intended for the 2nd, 4th, 7th, 11 months, and so on, consist of a twice weekly injection of daunorubicin and vincristine in doses respectively of 30 mg/m$^2$ and 2 mg/m$^2$ per injection, as well as daily absorption of prednisone for seven days. In addition, methotrexate is administered by spinal injection, at the rate of two injections during each reinduction and one monthly injection in between.

In a procedure designed for acute lymphoblastic leukaemias, 1.5 mg/m$^2$ of vincristine one day of a week, is prescribed; the same day and the day after, 20 mg/m$^2$ of daunorubicin are injected, while prednisone is administered during seven consecutive days at a dose of 100 mg/m$^2$. Depending on the cases, a total of one to six weekly courses have been made. In the presence of acute granulocytic forms, where the number of weekly courses varied from 2 to 3, the dosage of daunorubicin was 20 mg/m$^2$ per day during 3 consecutive days, in combination with methylglyoxal - bis - guanylhydrazone, at the rate of 100 mg/m$^2$ every other day.

We claim:
1. Method of inducing a remission in a human patient having acute leukaemia or chronicmyeloid leukaemia, said method comprising administering parenterally to said patient a remission-inducing amount of daunorubicin or of a non-toxic acid addition salt thereof.

2. Method according to claim 1 in which the daunorubicin or salt thereof is administered intravenously.

3. Method according to claim 2 in which the said patient has acute lymphoblastic leukaemia or acute myeloblastic leukaemia and daunorubicin is administered in a daily dose of 0.1 to 2 mg/kg for 2 to 8 days till the leucopenia reaches 1000 to 1500 units per mm$^3$.

4. Method according to claim 1 in which the said patient had chronic myeloid leukaemia and daunorubicin is administered every two or three days in a dose of 2 mg/kg.

* * * * *

UNITED STATES PATENT AND TRADEMARK OFFICE
CERTIFICATE OF CORRECTION

PATENT NO. : 3,997,663
DATED : December 14, 1976
INVENTOR(S) : Sylvie PINNERT et al It is certified that error appears in the above-identified patent and that said Letters Patent are hereby corrected as shown below:

Column 1, line 8, for "3,801,232" read
-- 3,997,662 --

Signed and Sealed this

Seventeenth Day of October 1978

[SEAL]

Attest:

RUTH C. MASON
Attesting Officer

DONALD W. BANNER
Commissioner of Patents and Trademarks